United States Patent [19]

Kumobayashi et al.

[11] Patent Number: 4,605,750
[45] Date of Patent: Aug. 12, 1986

[54] RHODIUM-PHOSPHINE COMPLEX

[75] Inventors: Hidenori Kumobayashi; Susumu Akutagawa, both of Kanagawa, Japan

[73] Assignee: Takasago Perfumery Co., Ltd., Tokyo, Japan

[21] Appl. No.: 651,123

[22] Filed: Sep. 17, 1984

[30] Foreign Application Priority Data

Sep. 16, 1983 [JP] Japan .................. 58-169283

[51] Int. Cl.⁴ ........................... C07F 15/00
[52] U.S. Cl. ......................... 556/7; 556/22; 556/23
[58] Field of Search ............ 260/429 R; 556/7, 22, 556/23

[56] References Cited

U.S. PATENT DOCUMENTS

| | | | |
|---|---|---|---|
| 3,798,241 | 3/1974 | Kagan et al. | 549/221 |
| 3,939,188 | 2/1976 | McVicker | 260/429 R |
| 3,949,000 | 4/1976 | Violet | 260/429 R X |
| 4,008,281 | 2/1977 | Knowles et al. | 260/429 R X |
| 4,152,344 | 5/1979 | Unruh | 260/439 R X |
| 4,201,714 | 5/1980 | Hughes | 260/429 R X |
| 4,331,818 | 5/1982 | Riley | 568/17 |
| 4,374,278 | 2/1983 | Bryant et al. | 260/429 R X |
| 4,393,240 | 7/1983 | Stille | 260/429 R X |
| 4,397,787 | 8/1983 | Riley | 260/429 R |

OTHER PUBLICATIONS

JACS 106, pp. 5208–5217 (1984).
Angew. Chem. Int. Ed. Engl., 24, No. 3, pp. 217 to 219 (1985).

Primary Examiner—Helen M. S. Sneed
Attorney, Agent, or Firm—Sughrue, Mion, Zinn, Macpeak, and Seas

[57] ABSTRACT

A novel rhodium-phosphine complex represented by the formula (I):

$$[Rh(BINAP)_2]^+Y^-$$

wherein BINAP represents 2,2'-bis(diphenylphosphino)-1,1'-binaphthyl, and Y represents $ClO_4$, $PF_6$, $BF_4$, $PCl_6$ or $B(C_6H_4)$ is described. This complex can be used as a catalyst for various organic syntheses and also for asymmetric syntheses such as an asymmetric isomerization reaction and an asymmetric hydrogenation reaction. Due to its high activity, the complex is very useful as a catalyst.

1 Claim, 1 Drawing Figure

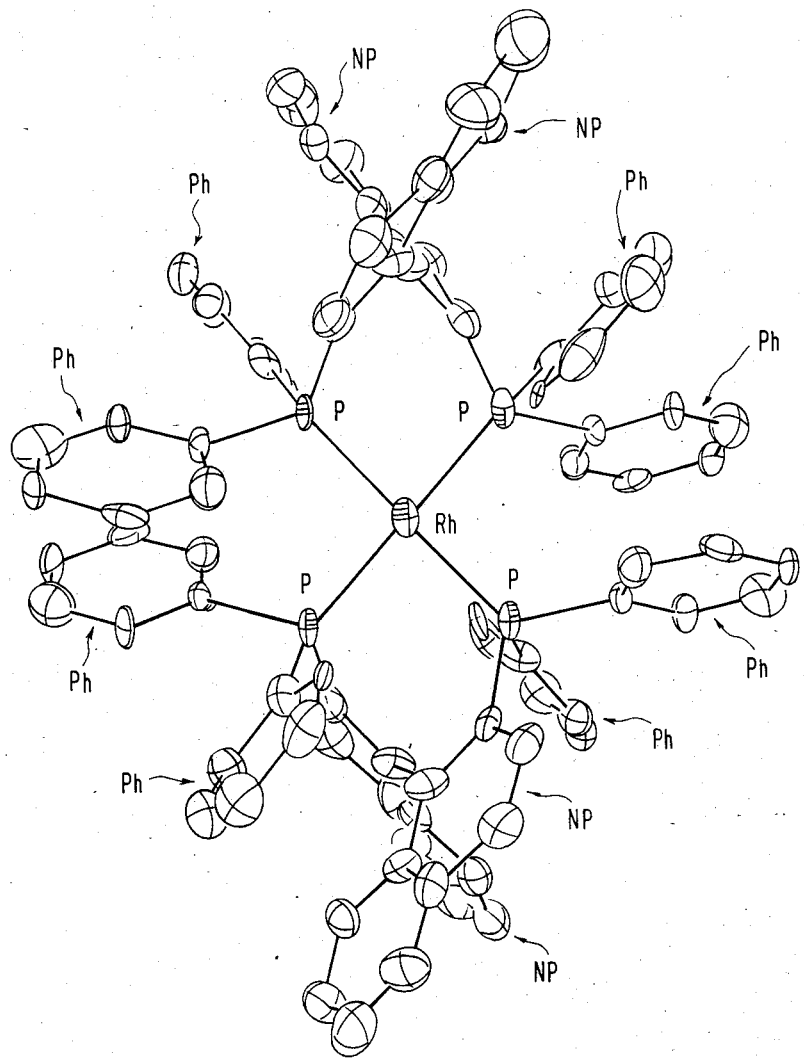

RHODIUM-PHOSPHINE COMPLEX

FIELD OF THE INVENTION

The present invention relates to a rhodium-phosphine complex. More particularly, it is concerned with a rhodium-phosphine complex which is used in preparation of various organic compounds and also in asymmetric syntheses such as an asymmetric isomerization reaction and an asymmetric hydrogenation reaction.

BACKGROUND OF THE INVENTION

Catalysts for use in organic syntheses have long been studied, and a variety of catalysts have been prepared and used for various purposes. Development of separation techniques of optically active substances has stimulated investigations on asymmetric syntheses and the results of such investigations have been published. Simultaneously, extensive studies on asymmetric catalysts for use in asymmetric syntheses such as an asymmetric isomerization reaction and an asymmetric hydrogenation reaction have been made in recent years.

Many transition metal complexes have heretofore been used as catalysts for preparation of organic compounds. In particular, noble metal complexes are stable and are easy to handle although those are expensive. Thus, extensive investigations are being made on organic syntheses utilizing such noble metal complexes as catalysts. In recent years, organic synthesis reactions which are impossible to perform by other techniques have been reported.

In general, rhodium, palladium and nickel catalysts with tert-phosphine as an optically active ligand provided thereto give good results. Japanese Patent Application (OPI) No. 61937/80, for example, discloses a rhodium/phosphine catalyst as an asymmetric hydrogenation catalyst, in which chiral phosphine is coordinated to rhodium. The term "OPI" as used herein means a "published unexamined Japanese patent application".

Japanese Patent Application (OPI) No. 4748/83 discloses a method of preparing enamines or imines by isomerization of allylamine derivatives using as an asymmetric isomerization catalyst a rhodium complex represented by the formula (II):

[Rh(olefin)L]$^+$X$^-$ wherein the olefin represents ethylene, 1,3-butadiene, norbornadiene or cycloocta-1,5-diene; X represents ClO$_4$, BF$_4$ or PF$_6$; and L represents two triarylphosphines or a trivalent phosphine compound represented by the formula (III):

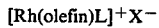

wherein Y is —(CH$_2$)$_3$—, —(CH$_2$)$_4$—, —(CH$_2$)$_5$—,

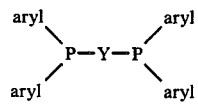

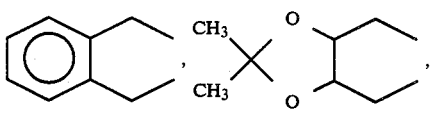

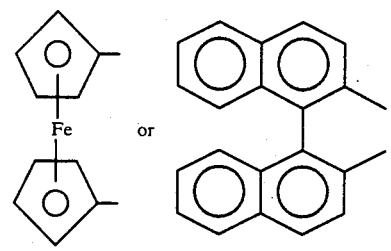

For example, neryldiethylamine is subjected to isomerization and the enamine thus prepared is hydrolyzed to obtain optically active citronellal.

Japanese Patent Application (OPI) No. 20294/84 describes a method of preparing a rhodium complex represented by the structural formula: [Rh(olefin)-BINAP]$^+$Y$^-$, and also a method of preparing (R)-3-methoxy-4-acetoxyphenylanine in high yield by asymmetic hydrogenation of 3-methoxy-4-acetoxyacetamidecinnamic acid using the rhodium complex catalysts.

These catalysts, however, have various disadvantages. One of the disadvantages is that their production costs are high since they are prepared using expensive metals and, furthermore, they are difficult to prepare and require a series of steps in preparation thereof. This results in increasing the price of the desired compound. Another disadvantage is that although their catalytic activity is high, such a high activity cannot be maintained for long periods of time, or conversely, although their catalytic life or durability is long, activity is relatively low. Thus, they are not suitable for use in industrial applications.

Under such circumstances, it has been desired to develop catalysts which are inexpensive, have a high activity and can maintain such a high activity for long periods of time.

SUMMARY OF THE INVENTION

Accordingly, the object of the present invention is to provide a novel rhodium-phosphine complex which can be used as a catalyst for various organic syntheses and also for asymmetric syntheses and, furthermore, which has a high activity and can maintain such a high activity for long periods of time.

A novel rhodium-phosphine complex useful as a catalyst according to the present invention is represented by the formula (I):

wherein BINAP represents 2,2'-bis(diphenylphosphino)-1,1'-binaphthyl; and Y represents ClO$_4$, PF$_6$, BF$_4$, PCl$_6$ or B(C$_6$H$_5$)$_4$.

BRIEF DESCRIPTION OF THE DRAWING

The FIGURE is a diagrammatic illustration of the structure of [Rh(BINAP)$_2$]$^+$ClO$_4^-$ as determined by X-ray analysis using a Model AFC C-4 Single Crystal Structure Analyzer and a rotor refractometer manufactured by Rigaku Denki Co., Ltd.

In the drawing, the symbols Ph and NP represent a phenyl group and a naphthyl group, respectively.

DETAILED DESCRIPTION OF THE INVENTION

The rhodium-phosphine complex of the present invention can be prepared in high yields by reacting a rhodium complex represented by the formula (IV):

[Rh(olefin)BINAP]+Y− wherein the olefin represents ethylene, 1,3-butadiene, cyclohexadiene, norbornadiene or cycloocta-1,5-diene; BINAP represents 2,2'-bis(diphenylphosphino)-1,1'-binaphthyl; and Y represents $ClO_4$, $PF_6$, $BF_4$, $PCl_6$ or $B(C_6H_5)_4$, with one mole of BINAP in a solvent such as tetrahydrofuran or acetone.

In one embodiment of the present invention, a rhodium complex of the formula (IV) is dissolved in a suitable solvent, an equimolar or excess amount of BINAP is added thereto, and the resulting uniform solution is then hydrogenated in an atmospheric pressure hydrogenating apparatus. This hydrogenation is carried out at a temperature of from 10° to 50° C. The time required for the hydrogenation process is from 1 to 10 hours. The reaction is determined to be completed when hydrogen absorption finishes. The pressure of hydrogen may be subatmospheric pressure as low as 5 atmospheric pressure or less. Thereafter, when hydrogen in the number of moles equal to that of rhodium is absorbed, the reaction is completed. The solvent is then distilled away from the reaction mixture, thereby obtaining the novel complex of the formula (I) of the present invention in a crystal form. Industrially the reaction mixture can be directly used, i.e., without distilling away the solvent. Solvents which can be used include tetrahydrofuran, acetone and dichloromethane.

In another embodiment, the novel complex of the present invention can be prepared as follows:

A rhodium complex of the formula (IV) is dissolved in a solvent such as tetrahydrofuran or acetone, and an equimolar or excess amount of BINAP to the rhodium complex is added thereto. The resulting mixture is heated to 50° to 60° C. After the reaction is completed, the solvent is distilled away. A fresh solvent is again added to prepare a uniform solution, and then the same reaction as above is repeated. The solvent is distilled away under reduced pressure. This operation is repeated two to four times, thereby obtaining the complex of the formula (I).

A racemic substance and/or an optically active substance of BINAP required to prepare the complex (I) of the present invention can be prepared by the method described in Japanese Patent Application No. 30799/83. That is, bromine and 1,1'-bi-2-naphthol are reacted using triphenylphosphine as a reaction aid to prepare 2,2'-dibromo-1,1'-binaphthyl, and the resulting 2,2'-dibromo-1,1'-binaphthyl is then reacted with chlorodiphenylphosphine in the presence of tert-butyllithium, whereupon the desired BINAP is obtained. The optically active substance can be prepared by acting d- or l-camphor-10-sulfornic acid or d- or l-3-bromocamphor-10-sulfonic acid as an optical resolution agent onto 2,2'-bis(diphenylphosphino)-1,1'-binaphthyldioxide which is obtained by oxidation of BINAP.

The rhodium complex of the formula (IV) can be prepared by the method described in Japanese Patent Application (OPI) No. 20294/84. That is, the rhodium complex can be easily prepared by reacting rhodium trichloride with an olefin such as cycloocta-1,5-diene in a solvent such as methanol or ethanol to prepare a rhodium/olefin complex, and then reacting the rhodium/olefin complex with BINAP as a trivalent phosphine compound.

The rhodium-phosphine complex of the present invention can be used as a catalyst for various organic syntheses and also for asymmetric syntheses such as an asymmetric isomerization reaction and an asymmetric hydrogenation reaction.

When the ligand does not have optical activity, the resulting rhodium-phosphine complex can be used as a catalyst for conventional organic syntheses. On the other hand, when it has optical activity, the resulting rhodium-phosphine complex can be used as an asymmetric synthesis catalyst.

One of the advantages of the present invention is that the rhodium-phosphine complex of the present invention has a high activity. That is, the activity of the rhodium-phosphine complex of the present invention is about 10 times those of conventionally used catalysts such as [Rh(cycloocta-1,5-diene)(BINAP)]+$ClO_4$− or [Rh(norbornadiene)(BINAP)]+$ClO_4$−. This contributes greatly to a reduction in production costs. The rhodium-phosphine complex similarly prepared using an optically active ligand is useful as a catalyst in asymmetric syntheses.

The following comparative example (Application Example 2) can be given to demonstrate the above-described significant effect, in which the rhodium-phosphine complex of the present invention is used in an isomerization reaction of allylamine.

Allylamine was isomerized using as a catalyst the rhodium-phosphine complex of the present invention, the molar ratio of allylamine to the complex being 4000:1 to 8000:1. In the subsequent reactions it was sufficient for the rhodium-phosphine complex to be supplemented in an amount of 1/10 of that added in the first reaction. On repeating this procedure, the allylamine in the amount of about 80,000 times that of the rhodium-phosphine complex could be isomerized into enamine.

The present invention is described in greater detail by reference to the following examples and application examples.

EXAMPLE 1

14.5 g of [Rh(cycloocta-1,5-diene)(BINAP)]+$ClO_4$− was dissolved in 780 ml of tetrahydrofuran, and 9.68 g of BINAP was added thereto to prepare a uniform solution. This uniform solution was placed in an atmospheric pressure hydrogenating apparatus, and hydrogenation was carried out at 25° to 30° C. After 3 hours, absorption of hydrogen was not observed. At this point, the reaction was determined to be completed. The tetrahydrofuran was distilled away under reduced pressure to obtain 22.4 g of a reddish brown crystal.

The elemental analytical values of the complex thus prepared were as follows.

|  | C | H | P | Cl | Rh |
|---|---|---|---|---|---|
| Found | 73.00 | 4.42 | 8.60 | 2.24 | 8.3 |
| Calculated | 73.00 | 4.42 | 8.57 | 2.45 | 8.57 |

The structure of the complex was determined by X-ray analysis, and its diagramatical illustration is shown in the FIGURE.

EXAMPLE 2

9.5 g of [Rh(cyclohexa-1,3-diene)((—)BINAP)]$^+$PF$_6^-$ was dissolved in 1,000 ml of acetone, and 6.2 g of (—)BINAP was added thereto. The resulting mixture was stirred while heating at 50° to 60° C. for about 1 hour. The acetone was distilled away under reduced pressure. 500 ml of a fresh acetone was then added and the same procedure as above was repeated. The acetone was distilled away. 500 ml of a fresh acetone was again added and the same procedure as above was repeated. 14.9 g of the desired complex, [Rh((—)BINAP)$_2$]$^+$PF$_6^-$, was obtained. The elemental analytical values of the complex were as follows:

|  | C | H | P | Rh | F |
|---|---|---|---|---|---|
| Found | 70.78 | 4.29 | 10.39 | 6.9 | 7.49 |
| Calculated | 70.9 | 4.32 | 10.21 | 6.5 | 7.64 |

APPLICATION EXAMPLE 1

The air in a 1 liter pressure vessel was replaced by nitrogen. Under a nitrogen atmosphere, 10 ml (0.2 millimole) of a tetrahydrofuran solution of the complex [(Rh(BINAP)$_2$]$^+$ClO$_4^-$ prepared in Example 1, 200 ml of tetrahydrofuran and 330 g of N,N-diethylgeranylamine were placed in the vessel and reacted at 100° C. for 15 hours. After the reaction was completed, the reaction mixture was transferred into a distilling column. After the tetrahydrofuran was distilled away, the resulting residue was further distilled under reduced pressure to obtain 328 g of the isomerized product, citronellaldiethylenamine (purity, 98.5%).

To the distillation residue was added 10 ml of n-heptane. The mixture was sufficiently stirred and a n-heptane soluble portion was removed by filtration. 10 ml of n-heptane was added and the same procedure as above was repeated. Thereafter, 200 ml of tetrahydrofuran was added to the distilling column and the remaining catalyst was dissolved therein to prepare a uniform solution. This uniform solution was returned to the 1 liter pressure vessel. 1 ml (0.02 millimole) of a fresh catalyst solution was added, and 330 g of N,N-diethylgeranylamine was added. The second reaction was carried out, whereby citronellaldiethylemaine of the same purity as in the first reaction was obtained in nearly the same amount as in the first reaction.

Thereafter, the same procedure as above was repeated with the same results.

APPLICATION EXAMPLE 2

(Comparative Example)

The reaction of Application Example 1 was repeated except that the catalyst was replaced by [Rh(cycloocta-1,5-diene)(BINAP)]$^+$ClO$_4^-$.

The distillation residue was washed with n-heptane as in Application Example 1. 200 ml of tetrahydrofuran was added and the remaining catalyst was uniformly dissolved therein. Thereafter, 0.02 millimole (1/10 of the amount used in the first reaction) of the catalyst was added and, in addition, 330 g of N,N-diethylgeranylamine was added. The second reaction was carried out in the same manner as in Application Example 1.

After the reaction was completed, the reaction mixture was examined by GLC analysis. This analysis showed that the conversion was 23%; that is, the reaction mixture was a mixture of 77% of unreacted N,N-diethylgeranylamine and 23% of citronellaldiethylenamine.

APPLICATION EXAMPLE 3

20 ml (0.2 millimole) of a tetrahydrofuran solution of [Rh(BINAP)$_2$]$^+$PF$_6$, 200 ml of tetrahydrofuran and 272 g of N,N-diethyl-7-hydroxynerylamine were placed in a pressure vessel in the same manner as in Application Example 1. The resulting mixture was reacted at 110° C. for 16 hours. After the reaction was completed, the tetrahydrofuran was distilled away in the same manner as in Application Example 1 to obtain 269.5 g of 7-hydroxycitronellaldiethylenamine (purity, 96.5%).

As the same as in Application Example 1, the reaction could be performed repeatedly.

APPLICATION EXAMPLE 4

10 ml (0.2 millimole) of a tetrahydrofuran solution of [Rh(BINAP)$_2$]$^+$BF$_4^-$, 200 ml of tetrahydrofuran and 167.2 g of N,N-diethylnerylamine were placed in a pressure vessel in the same manner as in Application Example 1. The resulting mixture was reacted at 100° C. for 18 hours. A distillation was applied to yield 165 g of citronellaldiethylenamine (purity, 98%).

As the same as in Application Example 1, the reaction could be performed repeatedly.

The elemental analytical values of the complex used above were as follows:

|  | C | H | P | Rh | B | F |
|---|---|---|---|---|---|---|
| Found | 73.92 | 4.53 | 8.60 | 7.08 | 0.69 | 5.21 |
| Calculated | 73.65 | 4.46 | 8.65 | 7.18 | 0.75 | 5.3 |

APPLICATION EXAMPLE 5

70 ml (0.2 millimole) of a tetrahydrofuran solution of [Rh(BINAP)$_2$]$^+$B(C$_6$H$_5$)$_4^-$, 160 ml of tetrahydrofuran and 113 g of N,N-diethylprenylamine were placed in a pressure vessel in the same manner as in Application Example 1. The resulting mixture was reacted at 90° C. for 10 hours. A distillation was applied to yield 108 g of 3-methylbutylaldehydediethylenamine (purity, 97.3%).

As the same as in Application Example 1, the reaction could be performed repeatedly.

The elemental analytical values of the complex used above were as follows:

|  | C | H | P | Rh | B |
|---|---|---|---|---|---|
| Found | 80.81 | 5.13 | 7.62 | 6.05 | 0.58 |
| Calculated | 80.68 | 5.04 | 7.44 | 6.18 | 0.65 |

APPLICATION EXAMPLE 6

10 ml (0.2 millimole) of a tetrahydrofuran solution of [Rh(BINAP)$_2$]$^+$PCl$_6^-$, 250 ml of tetrahydrofuran and 363 g of N,N-diethyl-7-hydroxygeranylamine were placed in a pressure vessel in the same manner as in Application Example 1. The resulting mixture was reacted at 100° C. for 13 hours. A distillation was applied to yield 360 g of 7-hydroxycitronellalenamine (purity, 98%).

As the same as in Application Example 1, the reaction could be performed repeatedly.

The elemental analytical values of the complex used above were as follows:

|            | C     | H    | P    | Cl   | Rh    |
|------------|-------|------|------|------|-------|
| Found      | 66.12 | 4.15 | 9.63 | 6.21 | 13.11 |
| Calculated | 66.37 | 4.02 | 9.74 | 6.47 | 13.39 |

APPLICATION EXAMPLE 7

10 ml (0.2 millimole) of a tetrahydrofuran solution of [Rh(+)BINAP$_2$]$^+$ClO$_4$$^-$, 240 ml of tetrahydrofuran and 250 g of N,N-diethylnerylamine were placed in a pressure vessel in the same manner as in Application Example 1. The resulting mixture was reacted at 100° C. for 16 hours. A distillation was applied to yield 247 g of d-citronellaldiethylenamine (purity, 97%).

The optical rotation, $[\alpha]_D^{25}$, of the enamine was −76°, and the optical purity was 98%.

As the same as in Application Example 1, the reaction could be performed repeatedly.

APPLICATION EXAMPLE 8

10 ml (0.2 millimole) of a tetrahydrofuran solution of [Rh((−)BINAP)$_2$]$^+$ClO$_4$$^-$, 200 ml of tetrahydrofuran and 330 g of N,N-diethylgeranylamine were placed in a pressure vessel in the same manner as in Application Example 1. The resulting mixture was reacted at 100° C. for 16 hours. A distillation was applied to yield 327 g of d-citronellaldiethylenamine (purity: 98.5%; optical purity: 99%).

As the same as in Application Example 1, the reaction could be performed repeatedly.

While the invention has been described in detail and with reference to specific embodiments thereof, it will be apparent from one skilled in the art that various changes and modifications can be made therein without departing from the spirit and scope thereof.

What is claimed is:

1. A rhodium-phosphine complex represented by the formula (I):

$$[Rh(BINAP)_2]^+Y^- \qquad (I)$$

wherein BINAP represents 2,2'-bis(diphenylphosphino)-1,1'-binaphtyl; and Y represents ClO$_4$, PF$_6$, BF$_4$, PCl$_6$ or B(C$_6$H$_5$)$_4$.